US012765753B2

(12) United States Patent
Jang et al.

(10) Patent No.: US 12,765,753 B2
(45) Date of Patent: Oct. 20, 2026

(54) MAGNETIC FIELD GENERATION MODULE

(71) Applicant: IUCF-HYU (INDUSTRY-UNIVERSITY COOPERATION FOUNDATION HANYANG UNIVERSITY), Seoul (KR)

(72) Inventors: Gun Hee Jang, Seoul (KR); Dae Hee Lee, Seoul (KR); Seung Uk Kim, Seoul (KR); Sung Ho Park, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 225 days.

(21) Appl. No.: 18/710,116

(22) PCT Filed: Sep. 16, 2022

(86) PCT No.: PCT/KR2022/013920

§ 371 (c)(1),
(2) Date: May 14, 2024

(87) PCT Pub. No.: WO2023/043279

PCT Pub. Date: Mar. 23, 2023

(65) Prior Publication Data

US 2024/0423455 A1 Dec. 26, 2024

(30) Foreign Application Priority Data

Sep. 16, 2021 (KR) ........................ 10-2021-0124158

(51) Int. Cl.
*A61B 1/00* (2006.01)
*A61B 1/04* (2006.01)

(52) U.S. Cl.
CPC .......... *A61B 1/00158* (2013.01); *A61B 1/041* (2013.01)

(58) Field of Classification Search
CPC ..... A61B 1/00158; A61B 1/041; A61B 34/73; A61B 2034/731; A61B 2562/162
See application file for complete search history.

(56) References Cited

U.S. PATENT DOCUMENTS 8,114,012 B2 * 2/2012 Fujita ..................... A61B 1/041 600/102
9,339,170 B2 * 5/2016 Nishihara .............. A61B 1/041
(Continued)

FOREIGN PATENT DOCUMENTS

JP 2005-103091 A 4/2005
JP 6701590 B2 5/2020
(Continued)

OTHER PUBLICATIONS

International Search Report for PCT/KR2022/013920 dated Dec. 27, 2022.

*Primary Examiner* — Anh Tuan T Nguyen
*Assistant Examiner* — Jae Woo
(74) *Attorney, Agent, or Firm* — Sughrue Mion, PLLC

(57) ABSTRACT

A magnetic field generation module is disclosed. The magnetic field generation module comprises: a main core; at least one auxiliary core located adjacent to the main core; and an auxiliary core driver which moves the auxiliary core along the circumference of the main core by using the center axis of the main core as a shaft.

9 Claims, 10 Drawing Sheets

(56) References Cited

U.S. PATENT DOCUMENTS

| | | | | |
|---|---|---|---|---|
| 12,014,869 | B2 * | 6/2024 | Jang | A61B 34/35 |
| 2004/0138552 | A1 * | 7/2004 | Harel | A61B 1/00158 600/407 |
| 2005/0216231 | A1 * | 9/2005 | Aoki | A61B 1/041 702/183 |
| 2007/0016006 | A1 * | 1/2007 | Shachar | A61B 5/0507 600/407 |
| 2007/0191671 | A1 * | 8/2007 | Kawano | A61B 5/702 600/12 |
| 2007/0221233 | A1 * | 9/2007 | Kawano | A61B 5/073 128/899 |
| 2007/0270628 | A1 * | 11/2007 | Kawano | A61B 34/73 600/12 |
| 2008/0272873 | A1 * | 11/2008 | Reinschke | A61B 34/70 335/299 |
| 2008/0300458 | A1 * | 12/2008 | Kim | A61B 34/73 600/118 |
| 2009/0299142 | A1 * | 12/2009 | Uchiyama | A61B 1/00057 600/118 |
| 2010/0305402 | A1 * | 12/2010 | Shachar | A61B 5/062 335/297 |
| 2011/0009697 | A1 * | 1/2011 | Kawano | A61B 1/041 600/117 |
| 2016/0213232 | A1 * | 7/2016 | Katayama | A61B 1/041 |
| 2018/0084976 | A1 * | 3/2018 | Duan | A61B 5/062 |
| 2019/0184545 | A1 * | 6/2019 | Jang | B25J 5/00 |
| 2020/0100658 | A1 * | 4/2020 | Abbott | A61B 1/0051 |
| 2021/0369093 | A1 * | 12/2021 | Duan | A61B 1/273 |
| 2021/0369373 | A1 * | 12/2021 | Zhang | A61B 34/30 |
| 2022/0061642 | A1 * | 3/2022 | Park | A61B 1/00158 |
| 2022/0122752 | A1 * | 4/2022 | Jang | A61B 34/35 |
| 2022/0199309 | A1 * | 6/2022 | Kim | A61B 5/062 |
| 2022/0246339 | A1 * | 8/2022 | Park | H01F 7/064 |
| 2024/0339254 | A1 * | 10/2024 | Jang | H01F 27/24 |
| 2025/0221610 | A1 * | 7/2025 | Jang | A61B 1/00158 |

FOREIGN PATENT DOCUMENTS

| | | | |
|---|---|---|---|
| KR | 10-0651199 | B1 | 12/2006 |
| KR | 10-1410214 | B1 | 6/2014 |
| KR | 10-2020-0115938 | A | 10/2020 |
| KR | 10-2021-0075599 | A | 6/2021 |
| KR | 10-2289065 | B1 | 8/2021 |
| WO | 2021/058601 | A1 | 4/2021 |

* cited by examiner

【Fig.1】
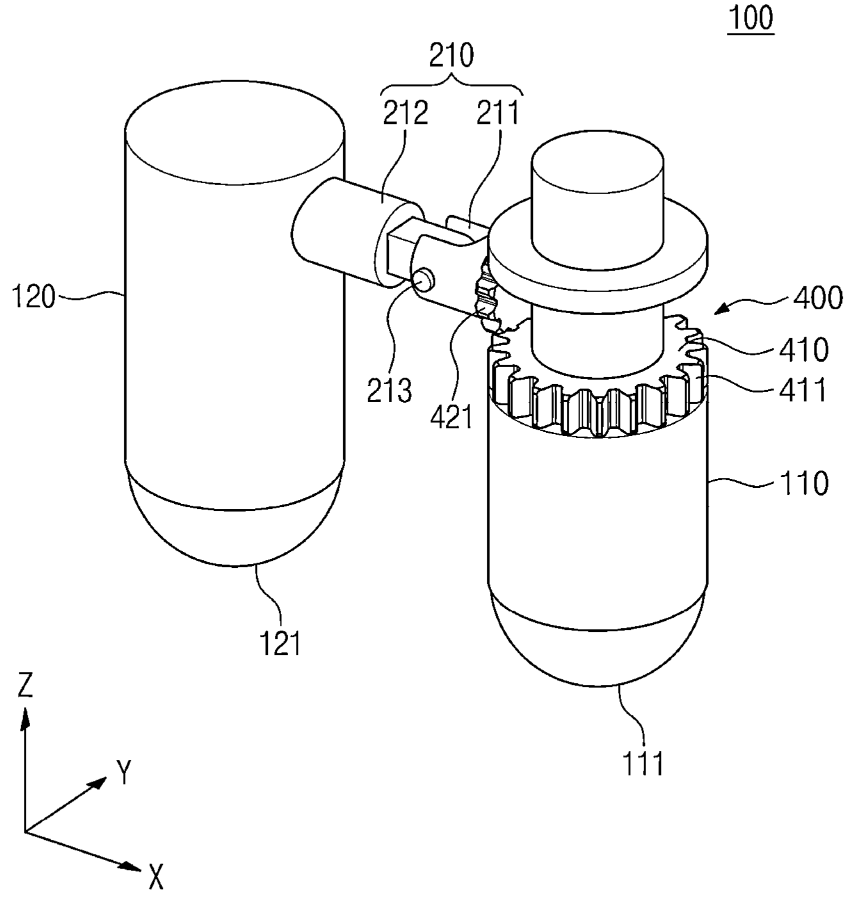

【Fig. 2】
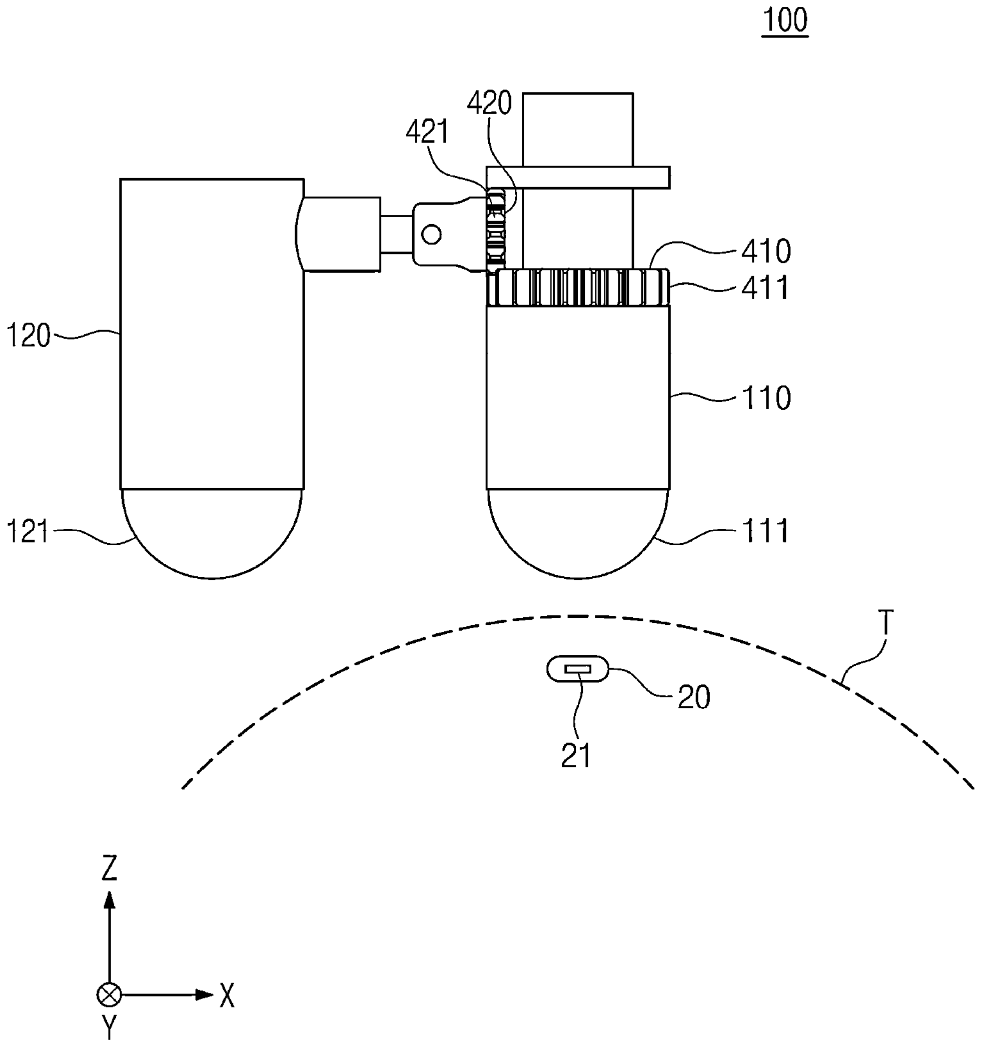

【Fig. 3】
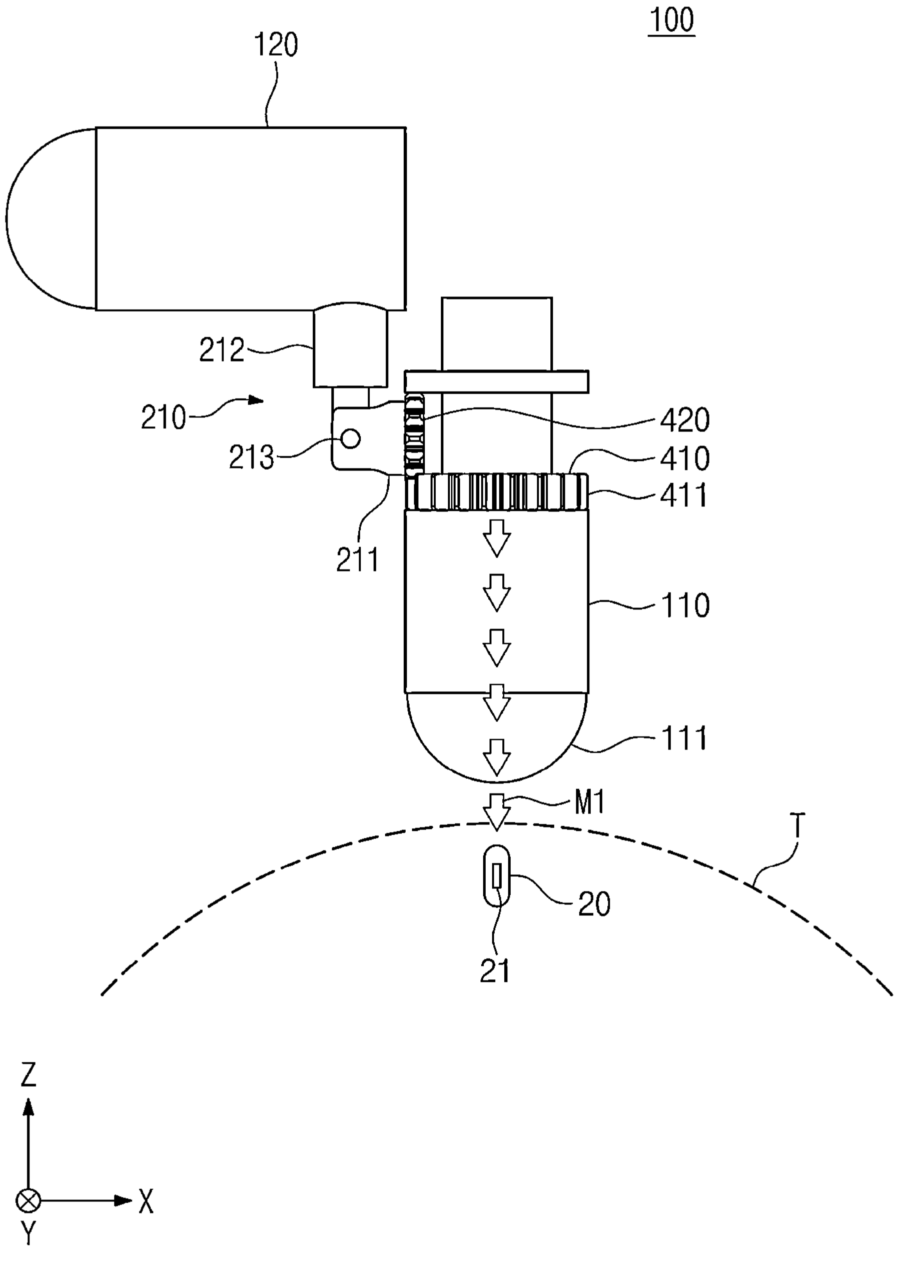

【Fig. 4】
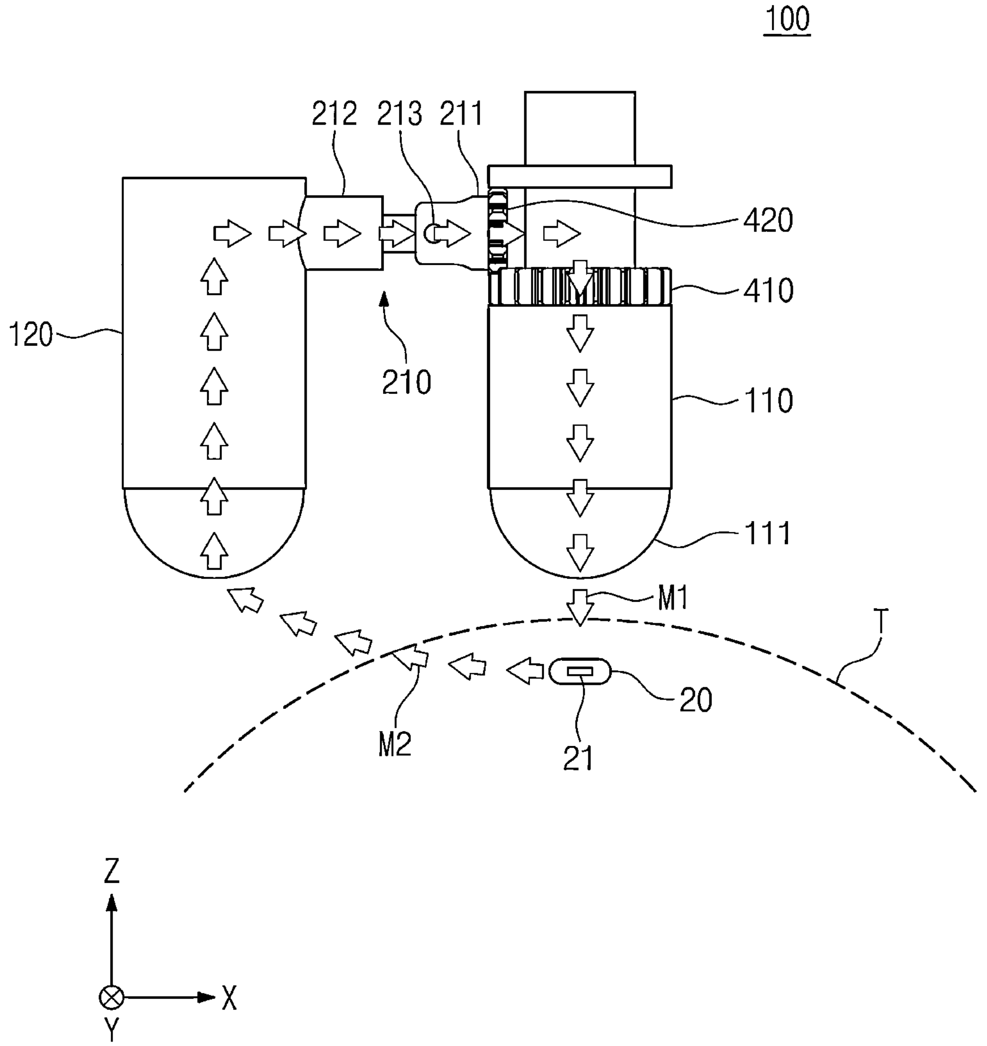

【Fig. 5】
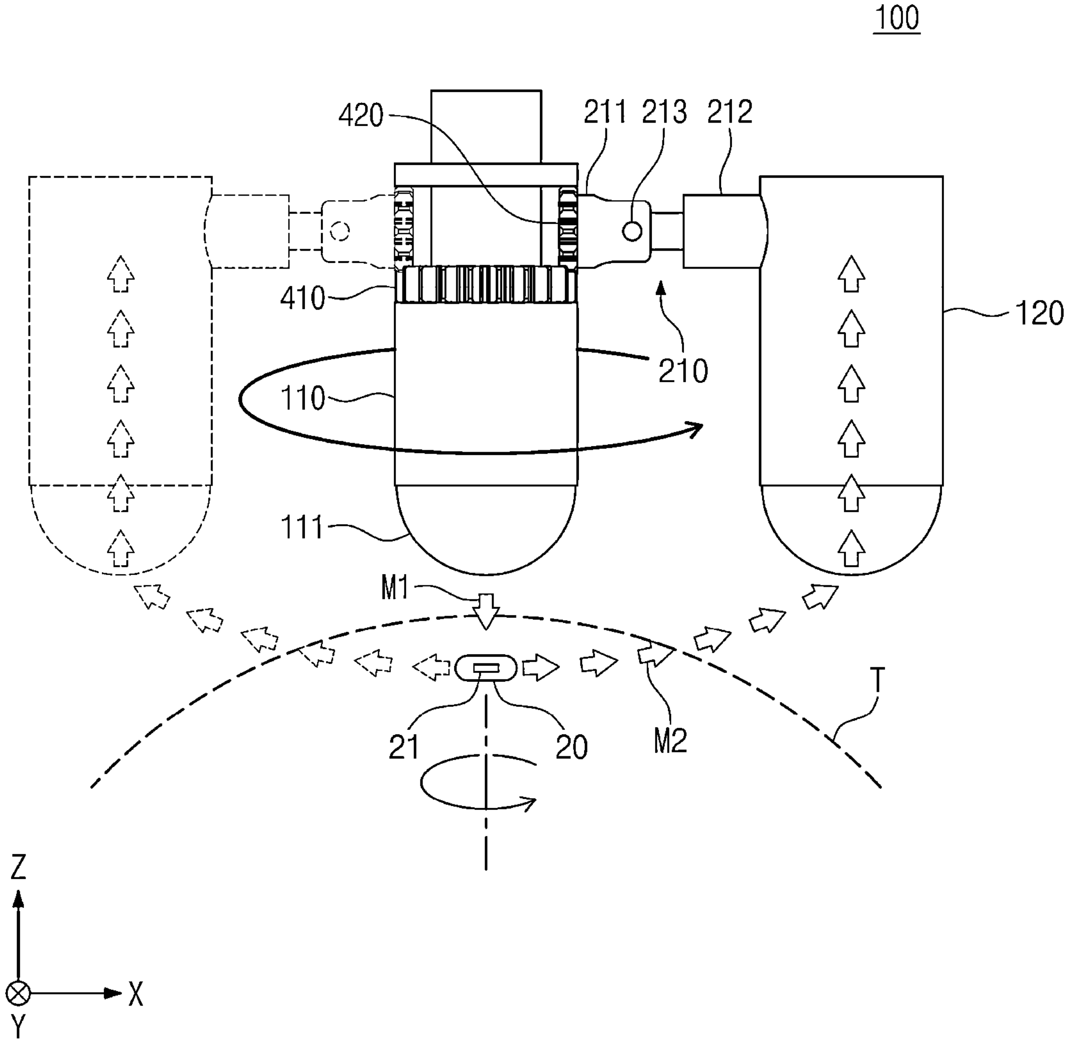

【Fig. 6】
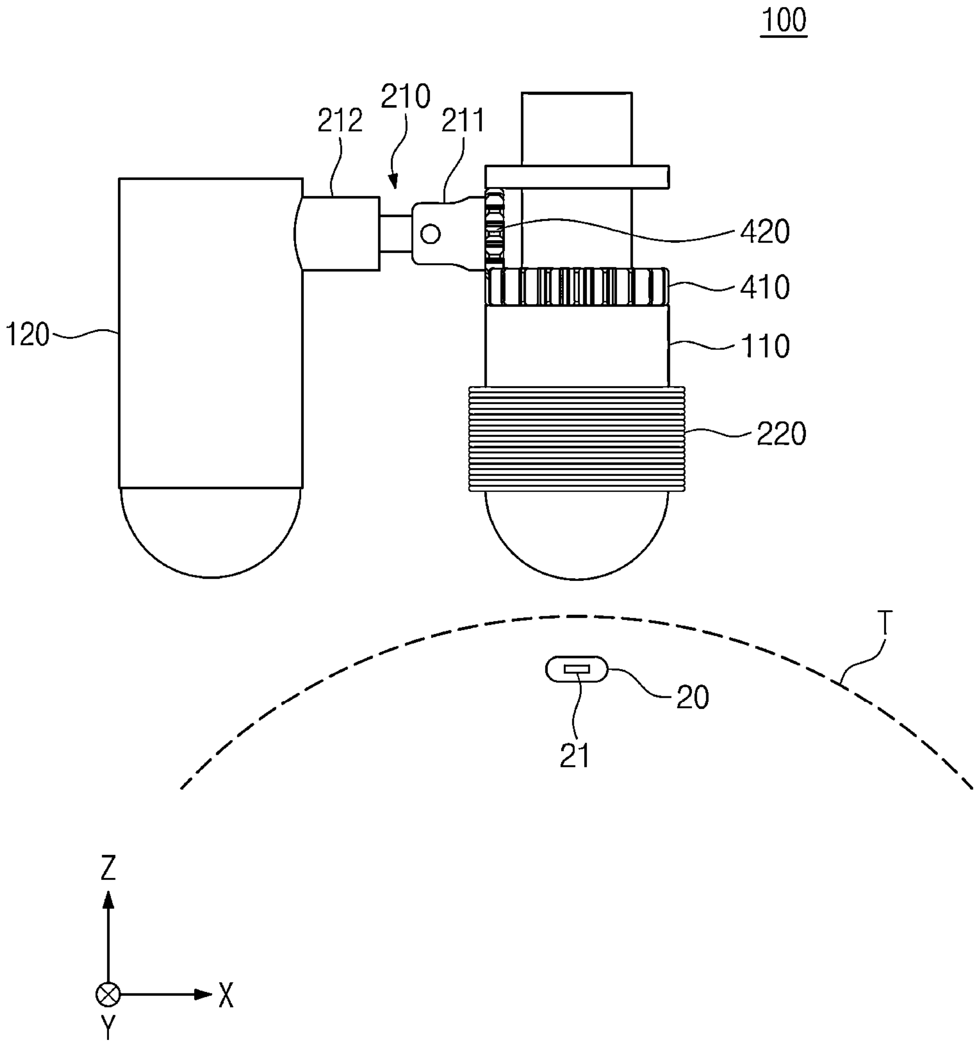

【Fig. 7】
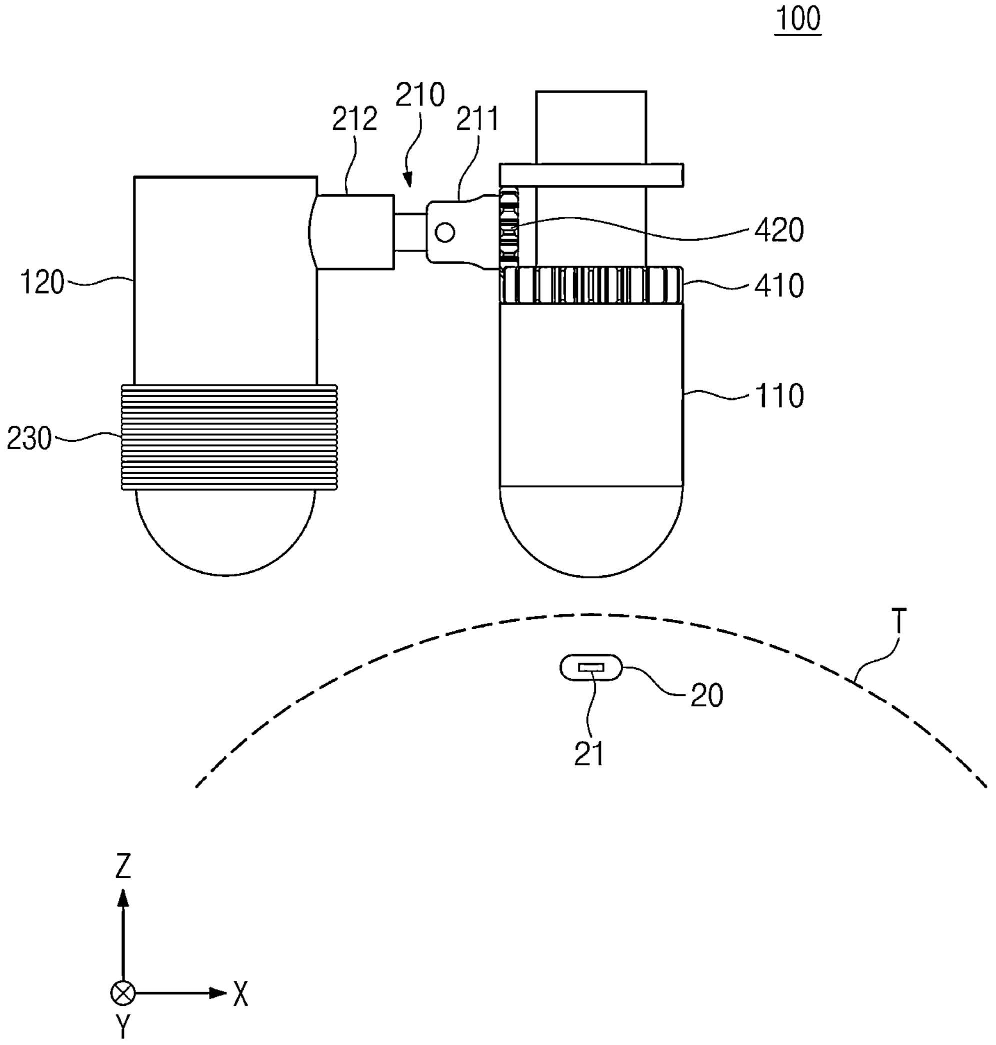

【Fig. 8】
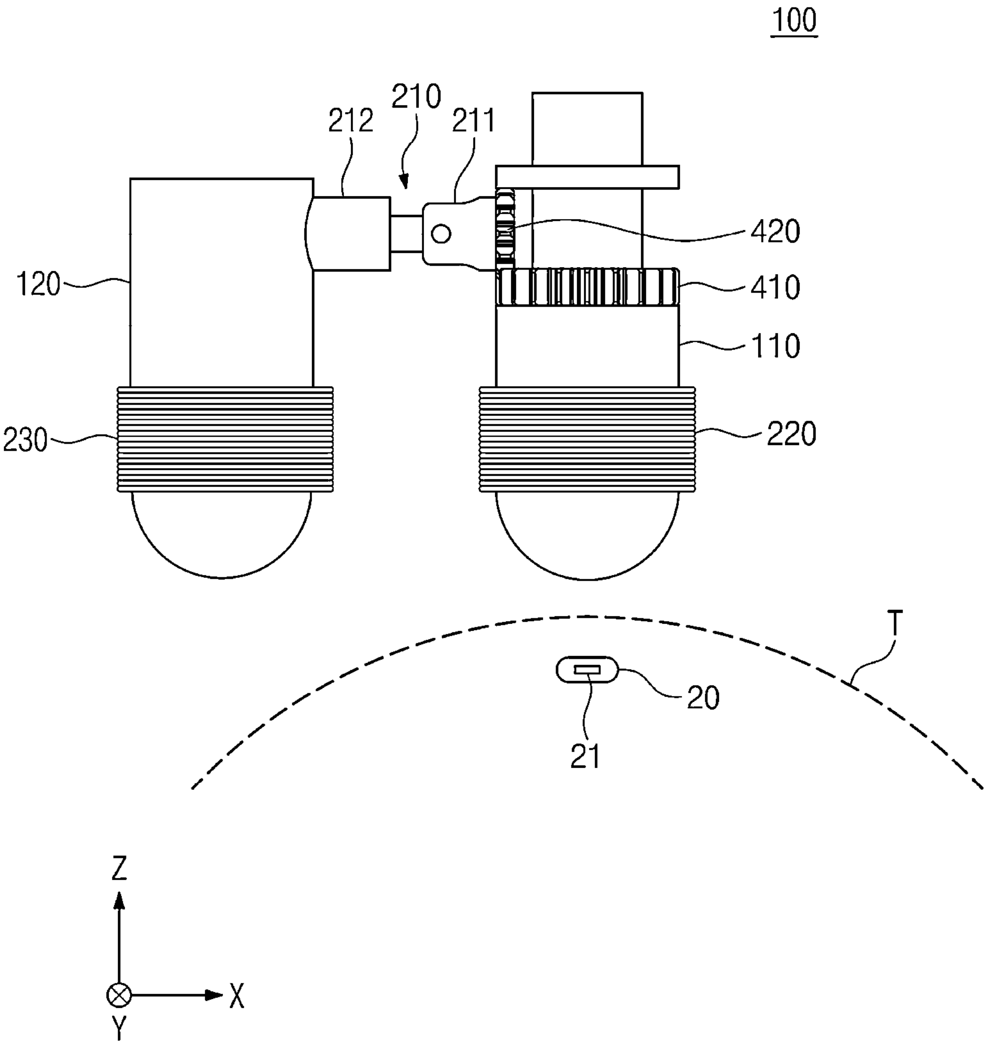

【Fig. 9】
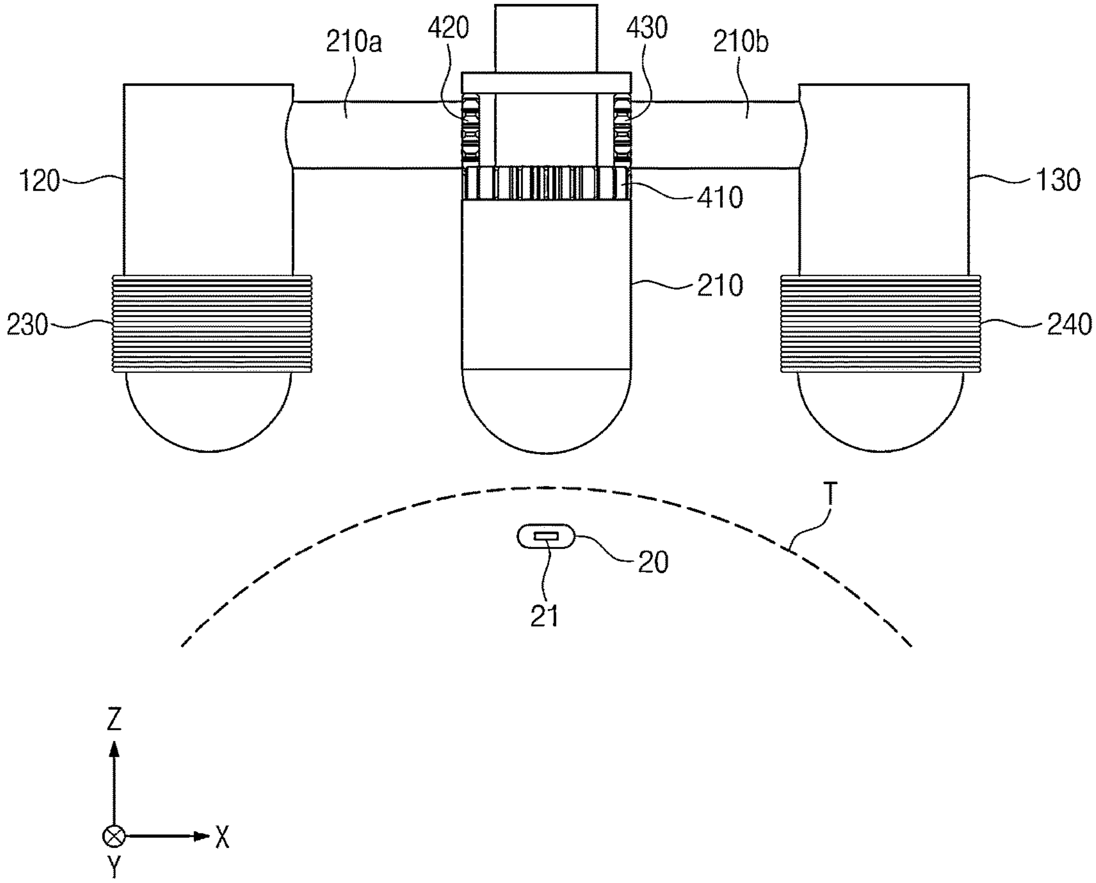

【Fig. 10】
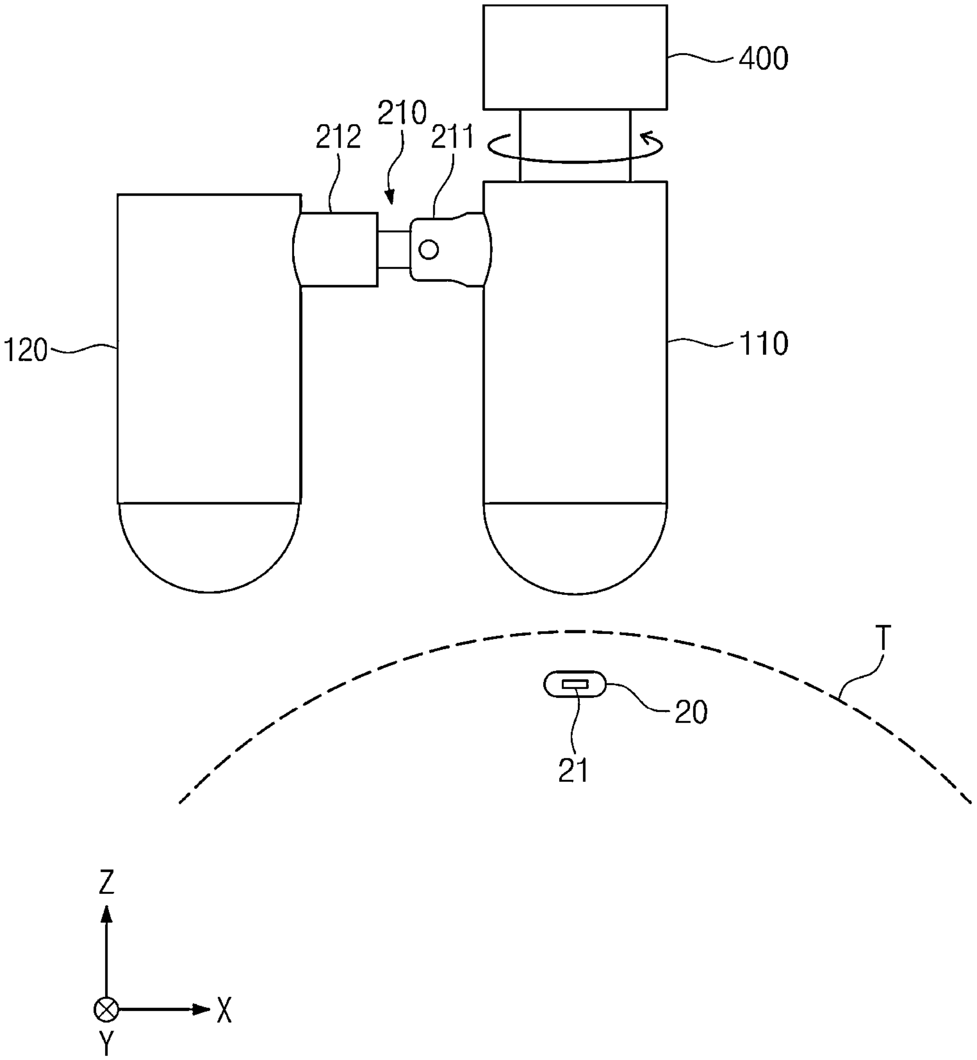

MAGNETIC FIELD GENERATION MODULE

CROSS REFERENCE TO RELATED APPLICATIONS

This application is a National Stage of International Application No. PCT/KR2022/013920 filed Sep. 16, 2022, claiming priority based on Korean Patent Application No. 10-2021-0124158 filed Sep. 16, 2021, the disclosure of which is incorporated by reference herein in its entirety.

TECHNICAL FIELD

The present invention relates to a magnetic field generation module, and more particularly, to a magnetic field generation module capable of controlling a posture of a capsule endoscope.

BACKGROUND ART

A medical capsule endoscope was developed to examine a digestive organ of a patient. Since an existing capsule endoscope has difficulty in examining a stomach having a large space, the existing capsule endoscope has been mainly used for performing a small intestine examination, in which it is difficult for a general endoscope to enter a small intestine, and an entire inner wall of the small intestine may be viewed only through peristalsis of a digestive organ, rather than examining an inner wall of the stomach.

However, there are cases where it is difficult for a capsule endoscope to pass through a region transiting from the stomach to a duodenum only through peristalsis of muscles. In addition, it is difficult to control a posture of the capsule endoscope in a desired direction, so that a medical staff has to check images captured from the capsule endoscope one by one, resulting in a longer examination time.

As described above, there are limitations in examining all regions of the digestive organ including an esophagus, a stomach, a duodenum, a small intestine, and a large intestine with the capsule endoscope. In order to overcome such limitations, researches for attaching a magnet to a capsule endoscope and controlling a movement of the capsule endoscope with an external magnetic field have recently been actively conducted at various research institutes.

DISCLOSURE

Technical Problem

The present invention provides a magnetic field generation module capable of controlling a posture of a capsule endoscope to examine all regions of a digestive organ including an esophagus, a stomach, a duodenum, a small intestine, a large intestine, and the like of a patient.

Technical Solution

According to the present invention, a magnetic field generation module includes: a main core; at least one auxiliary core located at a periphery of the main core; and an auxiliary core driving part for moving the auxiliary core along a circumference of the main core about a center axis of the main core.

In addition, the magnetic field generation module may further include: a core support part having a predetermined length, and having one end connected to the auxiliary core, and the auxiliary core driving part may include: a first gear having a ring shape, provided at a top of the main core, having a same center axis as the main core, and formed on an outer circumferential surface thereof with first teeth; a second gear coupled to an opposite end of the core support part, and formed on an outer circumferential surface thereof with second teeth engaged with the first teeth; and a driver for rotating the second gear about a center axis of the core support part.

In addition, the magnetic field generation module may further include: a core support part having a predetermined length, and having one end connected to the auxiliary core and an opposite end connected to the main core, and the auxiliary core driving part may rotate the main core about the center axis of the main core.

In addition, the core support part may include: a first region located toward the main core; and a second region rotatable relative to the first region, and configured to support the auxiliary core.

In addition, according to the rotation of the second region, the auxiliary core may be movable between a first position in which a center axis of the auxiliary core is arranged parallel to the center axis of the main core and a second position in which the center axis of the auxiliary core is arranged to be inclined with respect to the center axis of the main core.

In addition, the magnetic field generation module may further include: a main coil wound around the main core; an auxiliary coil wound around the auxiliary core; and a power supply unit for applying a current to the main coil and the auxiliary coil.

In addition, each of the main core and the auxiliary core may be formed of a hard magnetic material.

In addition, one of the main core and the auxiliary core may be formed of a hard magnetic material, and the remaining one of the main core and the auxiliary core may be formed of a soft magnetic material.

In addition, the magnetic field generation module may further include: a main coil wound around the main core; and a power supply unit for applying a current to the main coil, and the auxiliary core may be formed of a hard magnetic material or a soft magnetic material.

In addition, the magnetic field generation module may further include: an auxiliary coil wound around the auxiliary core; and a power supply unit for applying a current to the auxiliary coil, and the main core may be formed of a hard magnetic material or a soft magnetic material.

In addition, the auxiliary core may include: a first auxiliary core located on one side of the main core; and a second auxiliary core located on an opposite side of the main core, and the auxiliary core driving part may individually move the first auxiliary core and the second auxiliary core about the center axis of the main core.

Advantageous Effects

According to the present invention, a magnetic field generated from a magnetic field generation module can be controlled to control a posture of a capsule endoscope such that the capsule endoscope is located perpendicular to an inner wall of a digestive organ, located to be inclined with respect to a center axis of a main core, or rotated 360 degrees about the center axis of the main core, and all regions of the digestive organ can be captured.

DESCRIPTION OF DRAWINGS

FIG. 1 is a perspective view showing a magnetic field generation module according to one embodiment of the present invention.

FIG. 2 is a front view showing the magnetic field generation module of FIG. 1.

FIGS. 3 to 5 are views showing an operation process of a magnetic field generation module according to an embodiment of the present invention.

FIG. 6 is a view showing a magnetic field generation module according to another embodiment of the present invention.

FIG. 7 is a view showing a magnetic field generation module according to still another embodiment of the present invention.

FIG. 8 is a view showing a magnetic field generation module according to yet another embodiment of the present invention.

FIG. 9 is a view showing a magnetic field generation module according to still yet another embodiment of the present invention.

FIG. 10 is a view showing a magnetic field generation module according to another embodiment of the present invention.

BEST MODE

According to an embodiment of the present invention, a magnetic field generation module includes: a main core; at least one auxiliary core located at a periphery of the main core; and an auxiliary core driving part for moving the auxiliary core along a circumference of the main core about a center axis of the main core.

MODE FOR INVENTION

Hereinafter, exemplary embodiments of the present invention will be described in detail with reference to the accompanying drawings. However, the technical idea of the present invention is not limited to the embodiments described herein, but may be embodied in different forms. The embodiments introduced herein are provided to sufficiently deliver the idea of the present invention to those skilled in the art so that the disclosed contents may become thorough and complete.

When it is mentioned in the present disclosure that one element is on another element, it means that one element may be directly formed on another element, or a third element may be interposed between one element and another element. Further, in the drawings, thicknesses of films and regions are exaggerated for effective description of the technical contents.

In addition, although the terms such as first, second, and third have been used to describe various elements in various embodiments of the present disclosure, the elements are not limited by the terms. The terms are used only to distinguish one element from another element. Therefore, an element mentioned as a first element in one embodiment may be mentioned as a second element in another embodiment. The embodiments described and illustrated herein include their complementary embodiments, respectively. Further, the term "and/or" used in the present disclosure is used to include at least one of the elements enumerated before and after the term.

As used herein, an expression in a singular form includes a meaning of a plural form unless the context clearly indicates otherwise. Further, the terms such as "including" and "having" are intended to designate the presence of features, numbers, steps, elements, or combinations thereof described in the present disclosure, and shall not be construed to preclude any possibility of the presence or addition of one or more other features, numbers, steps, elements, or combinations thereof. In addition, the term "connection" used herein is used to include both indirect and direct connections of a plurality of elements.

Further, in the following description of the present invention, detailed descriptions of known functions or configurations incorporated herein will be omitted when they may make the gist of the present invention unnecessarily unclear.

FIG. 1 is a perspective view showing a magnetic field generation module according to one embodiment of the present invention, and FIG. 2 is a front view showing the magnetic field generation module of FIG. 1.

Referring to FIGS. 1 and 2, a magnetic field generation module 100 may generate and control a magnetic field and a magnetic force. The magnetic field and the magnetic force may be used to control a movement of a capsule endoscope 20 located within an operation region T. The capsule endoscope 20 may be inserted into a digestive organ of a human body so as to be used to examine the digestive organ, and may include a permanent magnet 21 provided inside the capsule endoscope 20. A posture of the capsule endoscope 20 may be controlled in a direction of the magnetic field by a magnetic torque formed by an interaction between the magnetic field generated from the magnetic field generation module 100 and the permanent magnet of the capsule endoscope 20.

The magnetic field generation module 100 may include a main core 110, an auxiliary core 120, a core support part 210, and an auxiliary core driving part 400.

The main core 110 may have a predetermined shape. The main core 110 may have a cylindrical shape or a polyprismatic shape having a predetermined length. The main core 110 may be formed of a hard magnetic material or a soft magnetic material. The hard magnetic material may refer to a material having a high magnetic permeability and a high coercive force, which may be used as a permanent magnet. Ferrite may be used as one example of the hard magnetic material. In addition to pure iron and silicon steel, an alloy having a high magnetic permeability or an alloy having a static magnetic permeability, such as a Fe—Ni-based alloy or a Fe—Al-based alloy, may be used as the soft magnetic material. According to an embodiment, the main core 110 may be formed of a ferromagnetic material to function as a permanent magnet. A bottom surface 111 of the main core 110 may be provided as a flat plane. Alternatively, a center region of the bottom surface of the main core 110 may protrude downward. The bottom surface of the main core 110 may be provided as a curved surface having a center region that is convex downward. Alternatively, the center region of the bottom surface of the main core 110 may be indented upward. The bottom surface of the main core 110 may be provided as a curved surface having a center region that is concavely indented upward. Due to such a shape of the main core 110, a magnetic flux density of a magnetic field generated from the main core 110 may be concentrated on the same line as a center axis of the main core 110.

The auxiliary core 120 may have a predetermined shape. The auxiliary core 120 may have a cylindrical shape or a polyprismatic shape having a predetermined length. The auxiliary core 120 may have the same diameter as the main core 110. Alternatively, the auxiliary core 120 may have a smaller diameter than the main core 110.

At least one auxiliary core 120 may be disposed at a periphery of the main core 110. The number of auxiliary cores 120 may vary. An example in which one auxiliary core 120 is provided at a periphery of the main core 110 will be described in the present embodiment. The auxiliary core 120 may be formed of a hard magnetic material or a soft magnetic material. When the auxiliary core 120 is formed of the hard magnetic material, a magnetic field formed in the main core 110, a magnetic field formed in the auxiliary core 120, and magnetic fields formed in the core support part 210 and the operation region T by magnetic forces of the main core 110 and the auxiliary core 120 may form a closed-loop magnetic field. In addition, when the auxiliary core 120 is formed of the soft magnetic material, the magnetic force of the main core 110 may be transmitted to the auxiliary core 120 and the core support part 210, and the magnetic fields formed in the main core 110, the core support part 210, and the auxiliary core 120, respectively, may form a closed-loop magnetic field together with the magnetic field formed in the operation region T.

A bottom surface 121 of the auxiliary core 120 may be provided in the same manner as the bottom surface 111 of the main core 110 described above. Alternatively, the bottom surface 121 of the auxiliary core 120 may be provided as an inclined surface in which one side and an opposite side have mutually different heights. The surface may be inclined toward the center axis of the main core 110, or may be inclined toward an outer side.

According to one embodiment, one side of the bottom surface 121 of the auxiliary core 120, which is adjacent to the main core 110, may be higher than an opposite side of the bottom surface 121. Accordingly, the bottom surface of the auxiliary core 120 may be inclined toward the center axis of the main core 110. A magnetic flux density of the magnetic field generated from the auxiliary core 120 may be concentrated on the opposite side of the bottom surface.

According to another embodiment, the one side of the bottom surface 121 of the auxiliary core 120, which is adjacent to the main core 110, may be lower than the opposite side of the bottom surface 121. Accordingly, the bottom surface of the auxiliary core 120 may be inclined toward the outer side. The magnetic flux density of the magnetic field generated from the auxiliary core 120 may be concentrated on the one side of the bottom surface.

The core support part 210 may be formed of a magnetic material, and may support the auxiliary core 120. The core support part 210 may have a predetermined length, and may have one end connected to the auxiliary core 120 and an opposite end located adjacent to the main core 110. According to an embodiment, the core support part 210 may be divided into a first region 211 and a second region 212. The first region 211 may be located toward the main core 110, and the second region 212 may be connected to the auxiliary core 120. The second region 212 may be coupled to the first region 211 through a shaft 213 so as to be rotatable relative to the first region 211. The second region 212 may rotate in a Z-direction about the shaft 213 that is perpendicular to a longitudinal direction of the core support part 210.

According to the rotation of the second region 212, the auxiliary core 120 may be movable between a first position in which a center axis of the auxiliary core 120 is arranged parallel to the center axis of the main core 110 and a second position in which the center axis of the auxiliary core 120 is arranged perpendicular to the center axis of the main core 110 or arranged to be inclined with respect to the center axis of the main core 110.

The auxiliary core driving part 400 may move the auxiliary core 120 along a circumference of the main core 110 about the center axis of the main core 110. According to an embodiment, the auxiliary core driving part 400 may include a first gear 410, a second gear 420, and a driver (not shown).

The first gear 410 may be coupled to the main core 110 at a top of the main core 110. The first gear 410 may have a ring shape having a predetermined diameter, and may have the same center axis as the main core 110. The first gear 410 may have the same diameter as the main core 110. The first gear 410 may be formed on an outer circumferential surface thereof with first teeth 411 formed along a circumference of the first gear 410.

The second gear 420 may be provided at the opposite end of the core support part 210, and may have a ring shape having a predetermined diameter. A center axis of the second gear 420 may be disposed in the longitudinal direction of the core support part 210, and disposed perpendicular to the center axis of the first gear 410. The second gear 420 may be formed on an outer circumferential surface thereof with second teeth 421, and the second teeth 421 may be engaged with the first teeth 411. The second gear 420 may rotate relative to the core support part 210 about the center axis of the second gear 420.

The driver may rotate the second gear 420. Although not shown in the drawings, the driver may be located inside the core support part 210.

According to driving of the driver, the second gear 420 may rotate about the center axis of the second gear 420. In addition, the second gear 420 may be engaged with the first gear 410 to move along the outer circumferential surface of the first gear 410. According to the movement of the second gear 420, the core support part 210 and the auxiliary core 120 may move along the circumference of the main core 110.

FIGS. 3 to 5 are views showing an operation process of a magnetic field generation module according to an embodiment of the present invention.

Referring to FIG. 3, the magnetic field generation module 100 may control the posture of the capsule endoscope 20 in a Z-axis direction. In detail, the second region 212 may rotate relative to the first region 211 in the Z-axis direction, so that the auxiliary core 120 may be located in the second position. In this state, when the main core 110 is located in an upper portion of the capsule endoscope 20, the magnetic field and the magnetic force of the main core 110 may be formed in the Z-axis direction, so that the posture of the capsule endoscope 20 may be controlled in the Z-axis direction.

Referring to FIG. 4, the magnetic field generation module 100 may control the posture of the capsule endoscope 20 to be inclined with respect to the Z-axis direction. According to the rotation of the second region 212, the auxiliary core 120 may be located in the first position. In this state, when the main core 110 is located in the upper portion of the capsule endoscope 20, the magnetic fields formed in the main core 110, the auxiliary core 120, and the core support part 210 and the magnetic field formed in the operation region in which the capsule endoscope 20 is located may form a closed-loop magnetic field. The posture of the capsule endoscope 20 may be controlled at an angle inclined toward the auxiliary core 120 by a magnetic field M1 formed in the Z-axis direction and a magnetic field M2 formed to be inclined with respect to the Z-axis direction in the closed-loop magnetic field. Due to the above control of the posture of the capsule endoscope 20, the capsule endoscope 20 may be fixed to be inclined with respect to a stomach wall. A size of the angle at which the capsule endoscope 20 is inclined may be controlled by adjusting a distance between the main core 110 and the auxiliary core 120 according to the rotation of the second region 212.

Referring to FIG. 5, the magnetic field generation module 100 may control the posture of the capsule endoscope 20 such that the capsule endoscope 20 may rotate about the center axis of the main core 110. While the main core 110 is located in the upper portion of the capsule endoscope 20, the posture of the capsule endoscope 20 may be controlled at the angle inclined toward the auxiliary core 120 as described in FIG. 4. In this state, according to driving of the auxiliary core driving part 400, the auxiliary core 120 may move along the circumference of the main core 110. The magnetic field formed in the operation region T may rotate about the center axis of the main core 110 according to the movement of the auxiliary core 120, and the posture of the capsule endoscope 20 may be change according to the rotation of the magnetic field. The capsule endoscope 20 may rotate 360 degrees about the center axis of the main core 110 in a rotation direction of the auxiliary core 120.

FIG. 6 is a view showing a magnetic field generation module according to another embodiment of the present invention.

Referring to FIG. 6, the main core 110 may be formed of a soft magnetic material, and the auxiliary core 120 may be formed of a permanent magnet. The magnetic field generation module 100 may further include a main coil 220, a power supply unit (not shown), and a control unit (not shown). The main coil 220 may be wound around the main core 110. The power supply unit may apply a current to the main coil 220, and the control unit may control the current applied to the main coil 220.

Due to the application of the current to the main coil 220, a magnetic field and a magnetic force may be formed at a periphery of the main core 110 in a Z-axis direction. A magnetic flux density may be concentrated on the same line as the center axis of the main core 110 in the center region of the bottom surface of the main core 110. When the current is applied while the auxiliary core 120 is located in the second position, the posture of the capsule endoscope 20 may be controlled in the Z-axis direction so as to be fixed perpendicular to a stomach wall. When the current is applied while the auxiliary core 120 is located in the first position, the posture of the capsule endoscope 20 may be controlled at an angle inclined toward the auxiliary core 120. In addition, when the auxiliary core 120 moves along the circumference of the main core 110 according to the driving of the auxiliary core driving part 400, the capsule endoscope 20 may rotate about the center axis of the main core 110 in the rotation direction of the auxiliary core 120.

FIG. 7 is a view showing a magnetic field generation module according to still another embodiment of the present invention.

Referring to FIG. 7, the main core 110 may be formed of a permanent magnet, and the auxiliary core 120 may be formed of a soft magnetic material. The magnetic field generation module 100 may further include an auxiliary coil 230, a power supply unit (not shown), and a control unit (not shown). The auxiliary coil 230 may be wound around the auxiliary core 120. The power supply unit may apply a current to the auxiliary coil 230, and the control unit may control the current applied to the auxiliary coil 230. When the current is applied to the auxiliary coil 230, a magnetic field and a magnetic force may be formed at a periphery of the auxiliary core 120. The magnetic field formed at the periphery of the auxiliary core 120 may form a closed-loop magnetic field together with the magnetic field formed at the periphery of the main core 110. As described above, the closed-loop magnetic field may control the angle of the capsule endoscope 20 to be inclined, or rotate the capsule endoscope 20.

FIG. 8 is a view showing a magnetic field generation module according to yet another embodiment of the present invention.

Referring to FIG. 8, each of the main core 110 and the auxiliary core 120 may be formed of a soft magnetic material, and the magnetic field generation module 100 may further include a main coil 220, an auxiliary coil 230, a power supply unit (not shown), and a control unit (not shown). The main coil 220 may be wound around the main core 110, and the auxiliary coil 230 may be wound around the auxiliary core 120. The power supply unit may individually apply a current to the main coil 220 and the auxiliary coil 230, and the control unit may control the current applied to the main coil 220 and the auxiliary coil 230.

When the posture of the capsule endoscope 20 is to be controlled in the Z-axis direction, the auxiliary core 120 may be located in the second position according to the rotation of the second region 212, and the current may be applied to the main coil 220. Due to the application of the current, a magnetic field and a magnetic force may be formed in the Z-axis direction at a periphery of the main core 110, so that the posture of the capsule endoscope 20 may be controlled in the Z-axis direction.

When the posture of the capsule endoscope 20 is to be controlled so as to be inclined with respect to the Z-axis direction, the auxiliary core 120 may be located in the second position according to the rotation of the second region 212, and the current may be applied to each of the main coil 220 and the auxiliary coil 230. Due to the application of the current, the magnetic fields formed in the main core 110, the auxiliary core 120, and the core support part 210 and the magnetic field formed in the operation region T in which the capsule endoscope 20 is located may form a closed-loop magnetic field. Due to the closed-loop magnetic field, the posture of the capsule endoscope 20 located in the operation region T may be controlled to be inclined with respect to the Z-axis direction.

When the posture of the capsule endoscope 20 is to be rotated about the center axis of the main core 110, the current may be applied to each of the main coil 220 and the auxiliary coil 230, and the auxiliary core driving part 400 may be driven to allow the auxiliary core 120 to move along the circumference of the main core 110. According to the movement of the auxiliary core 120, the closed-loop magnetic field may be rotated, so that the capsule endoscope 20 may be rotated.

FIG. 9 is a view showing a magnetic field generation module according to still yet another embodiment of the present invention.

Referring to FIG. 9, a plurality of auxiliary cores 120 and 130 may be provided. According to an embodiment, two auxiliary cores 120 and 130 may be provided, in which a first auxiliary core 120 may be located on one side of the main core 110, and a second auxiliary core 130 may be located on an opposite side of the main core 110. The first auxiliary core 120 may be connected to a first core support part 210*a*, and the second auxiliary core 130 may be connected to a second core support part 210*b*. Unlike the core support part 210 described above, the first and second core support parts 210*a* and 210*b* may be provided in the form of a single rod without being separated into a first region 211 and a second region 212. This is because the posture of the capsule endoscope 20 may be controlled in the Z-axis direction by blocking a current applied to auxiliary coils 230 and 240, so that the auxiliary core 120 does not have to be moved to the second position.

The auxiliary core driving part 400 may further include a third gear 430. The third gear 430 may have the same structure as the second gear 420, and may be engaged with the first gear 410. The third gear 430 may be located at an opposite end of the second core support part 210*b*, and may rotate relative to the second core support part 210*b* according to the driving of the driver.

The first auxiliary core 120 may move along the circumference of the main core 110 according to the rotation of the second gear 420, and the second auxiliary core 130 may move along the circumference of the main core 110 according to the rotation of the third gear 430. The auxiliary coils 230 and 240 may be wound around the first auxiliary core 120 and the second auxiliary core 130, respectively, and the current may be applied to each of the auxiliary coils 230 and 240 from the power supply unit. The current may be selectively applied to one of and 240, or may be the auxiliary coils 230 simultaneously applied to the two auxiliary coils 230 and 240. Alternatively, the application of the current to the two auxiliary coils 230 and 240 may be blocked.

The main core 110 may be formed of a permanent magnet. Alternatively, the main core 110 may be formed of a soft magnetic material, a main coil may be wound around the main core 110, and a magnetic field may be formed at a periphery of the main core 110 by a current applied to the main coil.

When the application of the current to the auxiliary coils 230 and 240 is blocked, the posture of the capsule endoscope 20 may be controlled in the Z-axis direction by the magnetic field formed in the main core 110. When the current is applied to one of the auxiliary coils 230 and 240, or the current is alternately applied to the auxiliary coils 230 and 240, the posture of the capsule endoscope 20 may be controlled to be inclined toward the auxiliary coil to which the current is applied. In addition, while the current is applied to the auxiliary coil, when the first and/or second auxiliary core 120 and/or 130 is moved, the capsule endoscope 20 may be rotated about the center axis of the main core 110.

FIG. 10 is a view showing a magnetic field generation module according to another embodiment of the present invention.

Referring to FIG. 10, the core support part 210 may have one end connected to the auxiliary core 120 and an opposite end connected to the main core 110. In addition, the auxiliary core driving part 400 may rotate the main core 110 about the center axis of the main core 110. According to the rotation of the main core 110, the core support part 210 may rotate together with the main core 110, and the auxiliary core 120 may move along the circumference of the main core 110. The capsule endoscope 20 may rotate according to the movement of the auxiliary core 120.

Although the exemplary embodiments of the present invention have been described in detail above, the scope of the present invention is not limited to a specific embodiment, and shall be interpreted by the appended claims. In addition, it is to be understood by a person having ordinary skill in the art that various changes and modifications can be made without departing from the scope of the present invention.

INDUSTRIAL APPLICABILITY

A magnetic field generation module according to the present invention may be used to control a posture of a capsule endoscope in examining all regions of a digestive organ including an esophagus, a stomach, a duodenum, a small intestine, a large intestine, and the like of a patient.

The invention claimed is:

1. A magnetic field generation module comprising:
a main core;
at least one auxiliary core located at a periphery of the main core;
an auxiliary core driving part for moving the auxiliary core along a circumference of the main core about a center axis of the main core; and
a core support part having a predetermined length, and having one end connected to the auxiliary core,
wherein the auxiliary core driving part includes:
a first gear having a ring shape, provided at a top of the main core, having a same center axis as the main core, and formed on an outer circumferential surface thereof with first teeth;
a second gear coupled to an opposite end of the core support part, and formed on an outer circumferential surface thereof with second teeth engaged with the first teeth; and
a driver for rotating the second gear about a center axis of the core support part.

2. The magnetic field generation module of claim 1, wherein the core support part includes:
a first region located toward the main core; and
a second region rotatable relative to the first region, and configured to support the auxiliary core.

3. The magnetic field generation module of claim 2, wherein, according to a rotation of the second region,
the auxiliary core is movable between a first position in which a center axis of the auxiliary core is arranged parallel to the center axis of the main core and a second position in which the center axis of the auxiliary core is arranged to be inclined with respect to the center axis of the main core.

4. The magnetic field generation module of claim 1, further comprising:
a main coil wound around the main core;
an auxiliary coil wound around the auxiliary core; and
a power supply unit for applying a current to the main coil and the auxiliary coil.

5. The magnetic field generation module of claim 1, wherein each of the main core and the auxiliary core is formed of a hard magnetic material.

6. The magnetic field generation module of claim 1, wherein one of the main core and the auxiliary core is formed of a hard magnetic material, and the remaining one of the main core and the auxiliary core is formed of a soft magnetic material.

7. The magnetic field generation module of claim 1, further comprising:
a main coil wound around the main core; and
a power supply unit for applying a current to the main coil,
wherein the auxiliary core is formed of a hard magnetic material or a soft magnetic material.

8. The magnetic field generation module of claim 1, further comprising:
an auxiliary coil wound around the auxiliary core; and
a power supply unit for applying a current to the auxiliary coil,
wherein the main core is formed of a hard magnetic material or a soft magnetic material.

9. The magnetic field generation module of claim 1, wherein the auxiliary core includes:

a first auxiliary core located on one side of the main core; and a second auxiliary core located on an opposite side of the main core, and the auxiliary core driving part individually moves the first auxiliary core and the second auxiliary core about the center axis of the main core.

* * * * *